United States Patent
Zhang et al.

(10) Patent No.: US 7,169,111 B2
(45) Date of Patent: Jan. 30, 2007

(54) MULTI-CHANNEL BLIND SYSTEM IDENTIFICATION FOR CARDIOVASCULAR MONITORING

(75) Inventors: Yi Zhang, St. Paul, MN (US); Haruhiko H. Asada, Lincoln, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 602 days.

(21) Appl. No.: 10/367,120

(22) Filed: Feb. 14, 2003

(65) Prior Publication Data

US 2003/0171682 A1 Sep. 11, 2003

Related U.S. Application Data

(60) Provisional application No. 60/356,813, filed on Feb. 14, 2002.

(51) Int. Cl.
*A61B 5/00* (2006.01)
*A61B 5/02* (2006.01)

(52) U.S. Cl. ............... 600/485; 600/500; 600/486; 600/504; 600/505; 600/526

(58) Field of Classification Search .............. None
See application file for complete search history.

(56) References Cited

U.S. PATENT DOCUMENTS

| | | | | |
|---|---|---|---|---|
| 6,010,457 A | * | 1/2000 | O'Rourke | 600/500 |
| 6,117,087 A | | 9/2000 | Kamm et al. | |
| 6,381,562 B2 | | 4/2002 | Keane | |
| 6,647,287 B1 | * | 11/2003 | Peel et al. | 600/513 |
| 2002/0177781 A1 | * | 11/2002 | Amano | 600/485 |
| 2003/0038090 A1 | * | 2/2003 | Gershenson | 210/767 |

OTHER PUBLICATIONS

Welkowitz, W. *Engineering Hemodynamics: Application to Cardiac Assist Devices: Second Edition*, New York University Press, New York (1987).

Liu, H. et al *A Deterministic Approach to Blind Equalization*, Conference Record of the Twenty-Seventh Asilomar Conference of Signals, Systems and Computers, vol. 1, pp. 751-755 (1993).

Kay, Steven M. *Fundamentals of Statistical Signal Processing: Estimation Theory*, pp. 59-62, 196-198, PTR Prentice-Hall Inc., Englewood Cliffs, NJ (1993).

(Continued)

*Primary Examiner*—Robert L. Nasser
(74) *Attorney, Agent, or Firm*—Bromberg & Sunstein LLP

(57) ABSTRACT

Multi-channel blind system identification is utilized to identify a patient's cardiac functions without catheterization. The approach is adaptive to each patient's cardiovascular system variations. The cardiac functions can be determined by formulating an auto-regression moving average model utilizing either finite impulse response systems or a group of infinite impulse response systems. Both of these models identify the system functions by solving a set of linear equations using the least-squares method. The system input is then identified by deconvolving the system output and the estimated impulse response of each channel. These models can be augmented to obtain an estimate of the maximum order of the cardiac functions when they are unknown a priori. The approach can also be modified to obtain the cardiac functions by first resolving the distinct dynamics associated with each channel, then determining the common dynamics and ultimately determining the system input.

13 Claims, 13 Drawing Sheets

OTHER PUBLICATIONS

Xu, et al *A Least-Squares Approach to Blind Channel Identification*, IEEE Transactions on Signal Processing, vol. 43, No. 12, pp. 2982-2993 (1995).

Stergiopulos, N., et al *Evaluation of Methods for Estimation of Total Arterial Compliance*, American Journal of Physiology, Heart Circulation Physiology, vol. 268(3), pp. H1540-H1548 (1995).

Abed-Meraim, et al *Blind System Identification*, Proceedings of the IEEE, vol. 85, No. 8, pp. 1310-1322 (1997).

Fetics, B. et al *Parametric Model Derivation of Transfer Function for Noninvasive Estimation of Aortic Pressure by Radial Tonometry*, IEEE Transactions on Biomedical Engineering, vol. 46, No. 6, pp. 698-706 (1999).

Zhang, Yi *Multi-channel Blind System Identification for Central Hemodynamic Monitoring*, Yi Zhang Ph.D. Thesis, Massachusetts Institute of Technology, (2002).

Hua, et al. *Blind system identification using multiple sensors*, Acoustics, Speech, and Signal Processing, 1995. ICASSP-95., 1995 International Conference in Detroit, MI, USA May 9-12, 1995, New York, NY, USA IEEE, pp. 3171-3174 (1995).

\* cited by examiner

MULTI-CHANNEL BLIND SYSTEM IDENTIFICATION FOR CARDIOVASCULAR MONITORING

The present application claims priority from U.S. Provisional Application, Ser. No. 60/356,813 filed Feb. 14, 2002, which is incorporated herein by reference.

TECHNICAL FIELD

The present invention pertains to a method for non-invasive monitoring of system outputs in order to determine a system's dynamics and common input. Such methods may be applied to specific applications such as diagnostic monitoring of the cardiovascular system on the basis of peripheral measurements obtained non-invasively on a continuous basis.

BACKGROUND OF THE INVENTION

Cardiovascular diseases (CVDs) have been the No. 1 killer in the United States for almost every year of the past century. CVDs are also prevalent all over the world, especially among the elderly. Therefore, a need exists to develop effective cardiovascular monitoring techniques that provide information for early diagnosis and treatment of CVDs. The ultimate goal of cardiovascular monitoring is to evaluate cardiac performance, i.e., how well the heart is functioning. This is traditionally done by an invasive, expensive, and sometimes dangerous catheterization procedure. Because of the disadvantages, doctors use catheterization only for critically ill patients.

When catheterization is not utilized, cardiac performance is evaluated from information obtained by noninvasive monitoring, as described in Fetics, B. et al., "Parametric Model Derivation of Transfer Function for Noninvasive Estimation of Aortic Pressure by Radial Tonometry", *IEEE Trans. on Biomed. Eng.*, Vol. 46, No. 6, pp. 698–706 (1999). In hospitals, doctors derive the cardiac information from noninvasive peripheral measurements based various auxiliary measurements. For example, four of the most frequently used vital signs in cardiovascular monitoring are heart rate, electrocardiogram signals, blood pressure and oxygen saturation. Doctors combine this information together with other observations to judge how well the patient's heart is working. There are two disadvantages with this method. First, the method is based solely on localized data, wherein systemic information is not utilized. Second, the method involves discrete monitoring since doctors and nurses can only check a patient's readings every few hours; thus dynamic information is not considered.

Utilizing current model-based techniques, the central pressure can be estimated by mathematically transforming peripheral pressure measurements that can be measured non-invasively. This is inverse monitoring. The objective is to extract information about the central cardiovascular system characteristics from peripheral noninvasive measurements. Inverse monitoring requires deriving a general model from the central system characteristics to the peripheral pressure. First, invasive central measurements and noninvasive peripheral measurements are taken for a group of subjects. Second, the transfer function for each subject in the group is identified. Finally, the average of all the transfer functions is used as a general model for predictions on other subjects. Inverse monitoring is better than traditional clinical monitoring in that it is model-based, and therefore more systematic. As well, it provides continuous monitoring, and therefore all the trends and dynamics can be captured. Inverse monitoring, however, has two major disadvantages. First, an invasive central measurement is still necessary to identify the individual transfer functions from the central pressure, system input, to the peripheral pressure, system output. Second, an averaged transfer function is used to predict the input from the output on a particular subject. Since the characteristics of a cardiovascular system are highly time-variable and subject-dependent, such a general model will not work well for everyone.

SUMMARY OF THE INVENTION

In accordance with particular embodiments of the present invention, a method is provided for evaluating cardiac performance in a body of a subject having a circulatory system. The method includes the steps of:

(a) measuring outputs of a plurality of sensors, each sensor deployed at a site of the circulatory system of the subject and providing a signal constituting a channel, each channel having an output;

(b) collecting a plurality of channel outputs from the plurality of channels at specified instants of time;

(c) expressing the plurality of channel outputs in terms of a finite set of auto-regression parameters by recursive solution of an estimation model for auto-correlation functions, thereby estimating an impulse response and transfer function for each channel;

(d) estimating an input by deconvolution based on the estimated impulse response and the plurality of channel outputs; and (e) updating the finite set of auto-regression parameters based on continued performance of steps (a), (b), (c), and (d) in a series in which new data points are included and earlier data points are disregarded. A computer program product may be used to carry out the steps of the method.

In accordance with an alternate embodiment of the invention, the step of measuring may include determining peripheral pressure at a plurality of peripheral sites of the circulatory system. Additionally, the step of expressing the channel outputs in terms of a finite set of auto-regression parameters may include solution using a least-squares algorithm; assuming that a transfer function is separable into low-frequency and high-frequency components; and, furthermore, may be based upon an infinite impulse response representation of the circulatory system.

In accordance with another embodiment of the invention, the step of expressing the channel outputs in terms of a finite set of auto-regression parameters may include estimating a maximum order of the auto-correlation functions by:

(a) over-estimating the maximum order of the auto-correlation function;

(b) estimating an impulse response and transfer function for each channel based upon the overestimated maximum order; and (c) estimating the maximum order of the auto-correlation functions from common singular values of the estimated impulse response and transfer function based upon the overestimated maximum order.

In accordance with further embodiments of the invention, the method may further include the steps of (a) estimating a common low-frequency pole from the plurality of channel outputs;

(b) designing a pre-high-pass filter based on the estimated common low-frequency pole and impulse response;

(c) filtering the plurality of channel outputs using the pre-high-pass filter to obtain pre-filtered outputs;

(d) estimating a high-frequency impulse response based on the pre-filtered outputs; and (e) combining the low-frequency impulse response and the high-frequency impulse response to obtain a complete estimated impulse response, used, as summarized above, to estimate the system input.

In accordance with still another embodiment of the invention, the input is an intermediate input that includes common dynamics of the plurality of channels, and the finite set of auto-regression parameters includes a subset of auto-regression parameters that are unique to each of the plurality of channel outputs. This embodiment also includes the steps of estimating the common dynamics of the plurality of channels based at least in part upon the intermediate input; estimating a system input by deconvolution using the common dynamics; and updating the estimates based upon the updated auto-regression parameters. The embodiment may also, when identifying the common dynamics of the plurality of channels, include use outputs of the plurality of sensors corresponding substantially to a diastole of a cardiac cycle; or assume the channels have a common low-frequency pole. Furthermore, the embodiment may include using an electrocardiogram signal to provide a reference for estimating the system input.

In another alternate embodiment of the invention, another method is provided for evaluating cardiac performance in a body of a subject having a circulatory system. The method has the following steps:

(a) measuring outputs of a plurality of sensors, each sensor deployed at a site of the circulatory system of the subject and providing a signal constituting a channel, each channel having an output;

(b) collecting a plurality of channel outputs from the plurality of channels at specified instants of time;

(c) identifying distinct dynamics of an impulse response and transfer function for each channel based at least in part upon the plurality of channel outputs;

(d) identifying an intermediate input by deconvolution of the distinct dynamics of the impulse response and transfer function from the plurality of channel outputs;

(e) identifying the common dynamics of the plurality of channels based at least in part upon the intermediate input; and (f) identifying the system input by deconvolution using the common dynamics of the plurality of channels. The embodiment may be practiced by deconvolving the combination of the common dynamics and distinct dynamics, for each channel, from the plurality of channel outputs, or by deconvolving the common dynamics from the intermediate input. A computer program product may be used to carry out the steps of the method.

In accordance with the another alternate embodiment of the invention, other embodiments include, with identifying the impulse response and transfer function for each channel, using a multi-channel BSI algorithm; identifying a unique impulse response and transfer function to within a scalar factor; or estimating a maximum order of the transfer functions by:

(a) over-estimating the maximum order of the transfer functions;

(b) estimating an impulse response and transfer function for each channel based upon the overestimated maximum order; and (c) estimating the maximum order of the transfer functions from common singular values of the estimated impulse response and transfer function for each channel based upon the overestimated maximum order.

More embodiments of the invention include, when identifying the common dynamics of the plurality of channels, using an auto-regression moving average model and identifying the auto-regressive coefficients by using outputs of the plurality of sensors corresponding substantially to a diastole of a cardiac cycle; or assuming the plurality of channels have a common low-frequency pole. As well, the step of identifying the system input may include using an electrocardiogram signal to provide a reference for estimating the input.

BRIEF DESCRIPTION OF THE DRAWINGS

The foregoing features of the invention will be more readily understood by reference to the following detailed description taken with the accompanying drawings.

DETAILED DESCRIPTION OF PREFERRED EMBODIMENTS AND DESCRIPTION OF THE DRAWINGS

Figure 1:
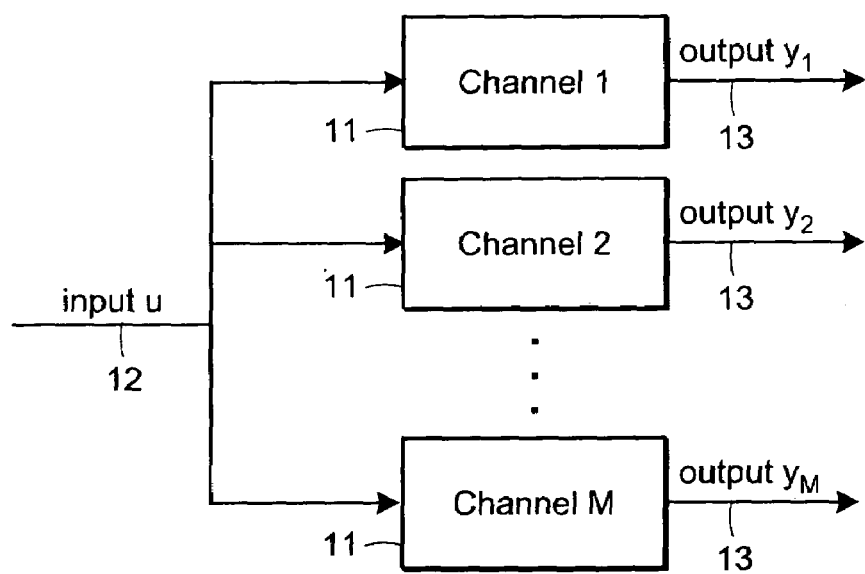
FIG. 1 provides a block diagram of a multi-channel system.

The invention will more readily be understood by reference to the following description taken with the accompanying drawings contained therein which depict adaptive cardiovascular multi-channel blind system identification as applied to a cardiovascular system, also depicted therein. The drawings are intended to provide a better understanding of the present invention, but are in no way intended to limit the scope of the invention.

In the following text, auto-regression parameters may be referred to as "AR" parameters, and moving average may be referred to as "MA", and thus auto-regression moving average may be denoted by the acronym "ARMA". Also, intermediate input identification may be denoted by the acronym "IIID".

Blind system identification (BSI) determines an unknown system function and the unknown system input solely from the system's output. One category of solutions to BSI exploits the statistical information of the input. However, a statistical model may not always be available, or there may not be enough data samples to find a reasonably accurate statistical estimate, which is the case for a cardiovascular system. Multi-channel BSI solves the blind identification problem by exploiting the cross relations inherent in multiple-output systems. The approach fits the topological structure of the cardiovascular system. In addition, with the advances in noninvasive cardiovascular sensing techniques, it is economically practical to implement noninvasive multi-channel cardiovascular monitoring.

New multi-channel BSI algorithms utilizing ARMA models are described herein and may advantageously provide accurate, inexpensive system monitoring techniques.

Formulation of the Multi-Channel BSI Problem for Cardiovascular Systems

The present invention encompasses non-invasive analysis of systems wherein data from a system's multiple outputs are utilized to obtain a system's dynamics and input. Though several of the embodiments described herein refer to the application of cardiovascular monitoring, the embodiments may be applied to an appropriate system where access to the system's outputs is readily available, but identification or estimation of the system's dynamics or input is less accessible. Non-limiting examples include determining a batch chemical reactor's temperature or concentration profiles from measurement of outflow effluent temperatures and concentration profiles; accurate estimation of a source signal which has suffered from distortion and noise during wireless communication; and pattern recognition.

In terms of a mathematical model, a system may be represented by a system function. For example, in a cardiovascular system, cardiac output is the system input and noninvasive peripheral measurements are the system output. The problem is whether both the system function and the system input can be determined given the system output. The problem is called blind system identification in that the system's input is not available to the signal processor. When there are multiple outputs, the problem is called multi-channel blind system identification.

FIG. 1, a block diagram of a multi-channel system, is used to show how to formulate a multi-channel BSI problem. The multiple channels 11 are driven by the system input 12, u, and yield different outputs 13, $y_1, \ldots, y_M$. Assuming that the channels 11 are linear and time-invariant, the system can be described by the following model:

$$\begin{cases} y_1 = h_1 * u \\ y_2 = h_2 * u \\ \vdots \\ y_M = h_M * u \end{cases} \quad (1)$$

where $h_1, \ldots, h_M$ denote the impulse response of each channel respectively, * denotes the linear convolution, and M denotes the number of channels. The multi-channel BSI problem is formulated as follows: Given the observations of the channel outputs $y_1, \ldots, y_M$, determine the channels' impulse responses $h_1, \ldots, h_M$, and ultimately recover the system input signal u.

The problem can be solved when the system is identifiable, as described by Abed-Meraim, el al., "Blind System Identification", *Proceedings of the IEEE*, Vol. 85, No. 12, pp. 1310–1332 (1997), which is incorporated herein by reference. The conditions for identifiability include:
1. All channels in the system must be distinct.
2. The input must be persistently excited.
3. The output must have enough samples available.

Figure 2:
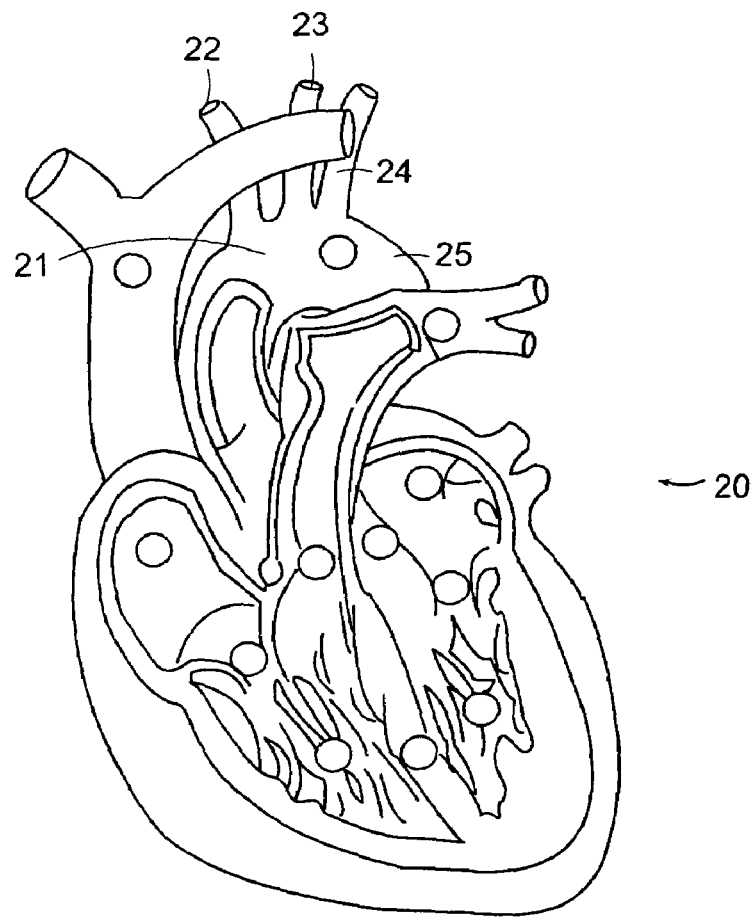
FIG. 2 illustrates the selected arteries of the human heart.

The circulatory system is inherently a multi-channel system. FIG. 2 shows the anatomy of the systemic circulation around the heart 20. All the systemic arteries branch from the aorta 21. The arch of the aorta 21 has three major branches: brachiocephalic trunk 22 supplying the right side of head and neck and the right upper limb, left common carotid artery 23 supplying the left side of head and neck, and left subclavian artery 24 supplying the left upper limb. After this branching, it becomes descending aorta 25, which further branches into arteries supplying organs and lower limbs.

Figure 3:
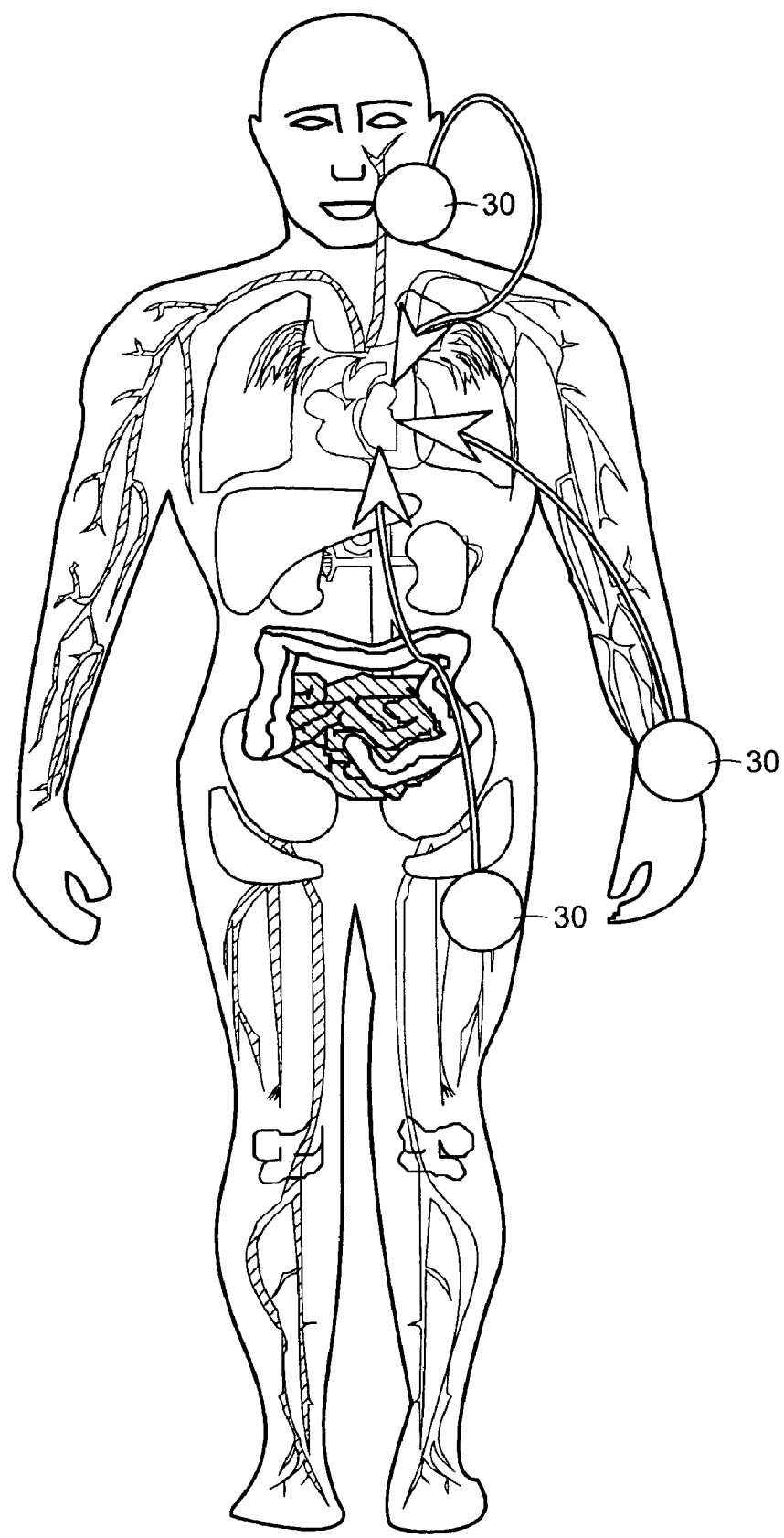
FIG. 3 provides a schematic of the placement of peripheral sensors used in the cardiovascular multi-channel BSI method.

If noninvasive sensors 30 are located at sites of the circulatory system, as illustrated in FIG. 3, the sensors' outputs are driven by the same input, which is cardiac output. When the system satisfies the identifiability conditions, the cardiac output can be estimated using multi-channel BSI. Compared to the inverse monitoring method, the multi-channel BSI method does not require invasive measurement. Furthermore, the method is tailored to each individual, thus the system functions identified are adapted to every person's unique cardiovascular system. The time variability of the cardiovascular system is also taken into account.

The cardiovascular system varies with time since it is regulated globally by the central nervous system and locally by metabolic need. Multi-channel BSI can be implemented in an online fashion to be adaptive to the time-variation. Each subject has a particular cardiovascular system estimator that is assumed to change slowly with respect to time, i.e. the time scale for system change may be of the order of hours or days. To identify the system, only a small window of data is utilized, the time scale of the window may be of the order of minutes. The system identification is continuously conducted based on a series of observations in different time windows. Within each window, a linear time-invariant system is assumed to simplify the algorithm, the model following the systemic features determined during the time window.

Therefore, this approach is adaptive to subjects' cardiovascular system variations.

For a cardiovascular system, the three identifiability conditions can be satisfied through:
1. Distinct channel characteristics: since different arteries have distinct mechanical properties, e.g. arterial compliance, different channels have distinct characteristics.
2. Persistently excited input: the aortic flow is similar to a periodic impulse function, which has very rich frequency components.
3. Enough output data: more data may be collected or the sampling rate may be increased.

An important practical issue is online detection of the identifiability of a system. Many current multi-channel BSI algorithms solve a set of linear equations (y=Ax) using the least-squares method ($\hat{x}=(A^T A)^{-1} A^T y$). Using this technique, the system identifiability detection problem is equivalent to the singularity problem of the matrix $A^T A$ that can be examined via singular value decomposition. Another practical issue is how to improve the identifiability of the system if it is unidentifiable. Since the identifiability is strongly affected by the locations of the zeroes in the system function, the identifiability can be improved by adjusting the locations of the sensors.

The Cross-Relation Solution Method: A Least-Squares BSI Algorithm for FIR Systems Generally, two types of systems are modeled: one with finite impulse response (FIR) and one with infinite impulse response (IIR). FIR often leads to simple development of signal processing algorithms. The assumption that a system function can be described by a FIR model is good for many practical applications, as an IIR system can be well approximated by a FIR model provided the order of the system function is large enough. If the order is too large, an IIR model is better since fewer system parameters are necessary. A BSI algorithm for FIR systems is described herein. For convenience, the solution to a two-channel system will be described, though the development for a multi-channel system is apparent to those skilled in the art.

Figure 4:
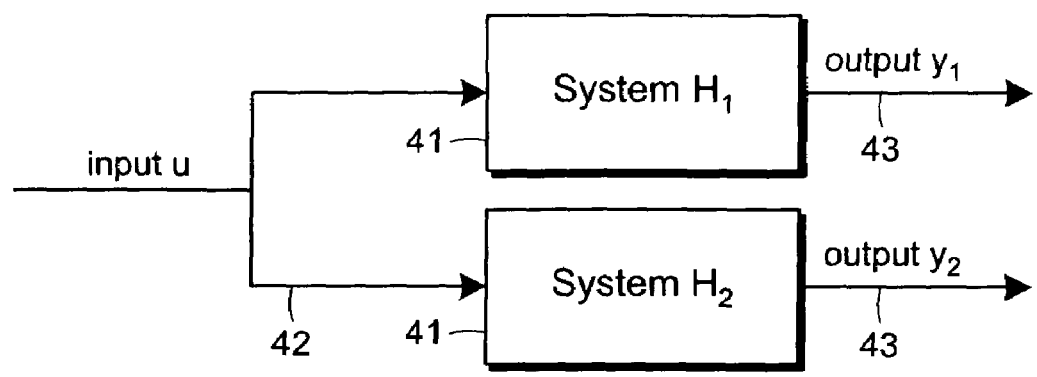
FIG. 4 provides a block diagram of a two-channel system with unknown input and unknown system functions.

Consider the two-channel system shown in FIG. 4. The two channels 41 are driven by the system input 42, u, and yield different outputs 43, $y_1$ and $y_2$. Assuming that the channels are linear and time-invariant, the system can be described by the following model:

$$\begin{cases} y_1(k) = \sum_{j=0}^{L} h_1(k)u(k-j) \\ y_2(k) = \sum_{j=0}^{L} h_2(k)u(k-j) \end{cases} \quad (2)$$

where L is the maximum order of the two channels. The two-channel BSI problem is formulated as follows: Given the observations of the channel outputs 43 $y_1$ and $y_2$, determine the channels' impulse responses $h_1$ and $h_2$, and the system input signal 42 u.

The outputs 43 from multiple channels 41 are correlated since they are driven by the same input 42. This correlation leads to a least-squares approach to BSI without requiring a priori knowledge of the system input, as described by Xu, G., et al., "A Least-squares approach to blind channel identification," *IEEE Transactions on Signal Processing*, Vol. 43, No. 12, pp. 2982–2993 (1995), which is herein incorporated by reference.

From eq. (2), for a two-channel system, the outputs $y_1(t)$ and $y_2(t)$ satisfy $$h_1(t)*y_2(t)=h_1(t)*(h_2(t)*u(t))=h_2(t)*(h_1(t)*u(t))=h_2(t)*y_1(t) \quad (3)$$

Both $h_1(t)$ and $h_2(t)$ have finite length, L, as determined by the maximum order of the two channels. Let N denote the number of input samples. The system input sequence can be denoted by u(n), n=0, ..., N; and the output sequence denoted by $y_i(n)$, n=L, ..., N. Thus, eq. (3) can be rewritten in matrix form:

$$[Y_1 - Y_2]\begin{bmatrix} h_2 \\ h_1 \end{bmatrix} = 0 \quad (4)$$

where, generally, $h_i \equiv [h_i(L), \ldots, h_i(0)]^T$, i=1,2 and $$Y_i \equiv \begin{bmatrix} y_i(L) & y_i(L+1) & \cdots & y_i(2L) \\ y_i(L+1) & y_i(L+2) & \cdots & y_i(2L+1) \\ \vdots & \vdots & \ddots & \vdots \\ y_i(N-L) & y_i(N-L+1) & \cdots & y_i(N) \end{bmatrix}^T, i = 1, 2$$

Eq. (4) can be solved using a least-squares method or singular value decomposition to solve all the channel responses simultaneously. This is known as the cross relation solution method to multi-channel BSI problem.

A Least-Squares BSI Algorithm for IIR Systems Using an ARMA Model

Figure 5:
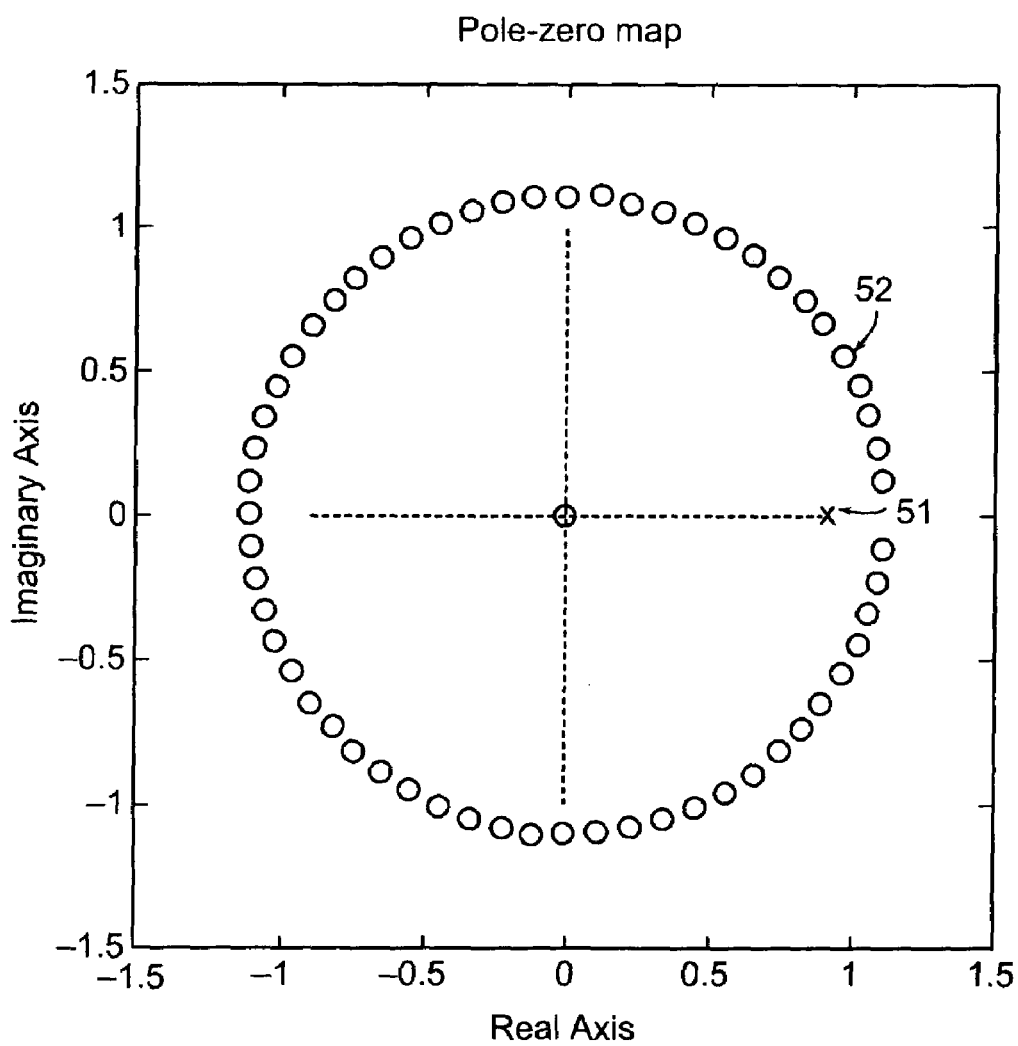
FIG. 5 provides a pole-zero map of a function and its FIR approximation.

Assuming that a system is accurately represented by FIR simplifies the development of the algorithms, but the assumption also presents difficulties. First, although approximating the system of interest by an FIR function may be reasonable when the system is stable, the approximation is often of very high order. For example, consider the system $H(z)=1/(z-0.9)$ with sampling rate 20 Hz. To approximate this system by an FIR, the impulse response must be truncated. Here the response is truncated at t=3 sec. FIG. 5 provides a graph of the poles of H(z), in the complex plane, for both the actual function 51 and the FIR representation 52. The actual H(z) has only one pole 51 at z=0.9. The FIR approximation, on the other hand, has 60 zeros 52.

Second, the order of the FIR approximation tends to increase as the sampling rate increases. For example, the order of the FIR approximation is doubled when the sampling rate is doubled. Finally, the zeros of the FIR approximation 52, as shown in FIG. 5, appear close to being equally spaced on a circle. This often leads to a numerically ill-conditioned identification problem.

In contrast, the IIR representation is more efficient, often requiring substantially fewer parameters and eliminating the problems mentioned earlier. A new approach for blind identification of a group of IIR systems that can be represented by auto-regression, moving average (ARMA) models is developed. Again, the algorithm will be described for a two-channel system and can be easily extended to multi-channel systems by those skilled in the art.

Consider the two-channel system shown in FIG. 4. The two channels 41 are driven by the system input 42, u, and yield two different outputs 43, $y_1$, $y_2$. Assuming that the channels 41 are linear and time-invariant, the system can be described using an ARMA model as follows:

$$y_i(n) + \sum_{k=1}^{p} a_k y_i(n-k) = \sum_{k=0}^{q} b_{ik} u(n-k), i = 1, 2 \quad (5)$$

where $a_1, \ldots, a_p$ denote the AR parameters; $b_{i1}, \ldots, b_{iq}$ (i=1, 2) denote the MA parameters; p denotes the number of poles; and q denotes the number of zeros. Here, the AR parameters are identical for the two channels 41. This is common when sensors are located at different branches of the same system, such as the cardiovascular system. The transfer functions can be written as $$H_i(z) = \frac{Y_i(z)}{U(z)} = \frac{B_i(z)}{A(z)}, i = 1, 2 \qquad (6)$$

where $$A(z) = 1 + \sum_{k=1}^{p} a_k z^{-k}, B_i(z) = \sum_{k=0}^{q} b_{ik} z^{-k}, i = 1, 2. \qquad$$

The BSI problem is formulated as follows: Given the observations of the channel outputs $y_1(n)$, $y_2(n)$, $n=1, \ldots, N$, determine the AR parameters $a_1, \ldots, a_p$ and the MA parameters $b_{i1}, \ldots, b_{iq}$ (i=1, 2) and ultimately recover the system input signal $u(n)$, $n=1, \ldots, N$.

The estimation of the AR parameters is achieved by solving the modified Yule-Walker equations, as described in Kay S. M., *Fundamentals of Statistical Signal Processing: Estimation Theory*, Prentice Hall, Upper Saddle River, N.J. (1993), which is incorporated herein by reference. Assuming that u is white noise with zero mean and that the system is causal, the auto-correlation functions of the outputs, $r_{y_1 y_1}(n)$, $r_{y_2 y_2}(n)$, satisfy the modified Yule-Walker equations:

$$r_{y_i y_i}(n) + \sum_{k=1}^{p} a_k r_{y_i y_i}(n-k) = 0, i = 1, 2 \text{ for } n > q \qquad (7)$$

In practice, the auto-correlation functions can be estimated by $$\hat{r}_{y_i y_i}(k) = \frac{1}{N} \sum_{n=1}^{N-1-|k|} y_i(n) y_i(n+|k|), i = 1, 2 \qquad (8)$$

A particular estimation model for $r_{y_i y_i}(k)$ can be formulated by replacing $r_{y_i y_i}(k)$ with $\hat{r}_{y_i y_i}(k)$. Thus, eq. (7) can be used as a linear prediction model of the AR parameters in the form of $x_i = H_i \theta + e_i$ (i=1,2):

$$\begin{bmatrix} \hat{r}_{y_i y_i}[q+1] \\ \vdots \\ \hat{r}_{y_i y_i}[M] \end{bmatrix} = \begin{bmatrix} \hat{r}_{y_i y_i}[q] & \cdots & \hat{r}_{y_i y_i}[q-p+1] \\ \vdots & \ddots & \vdots \\ \hat{r}_{y_i y_i}[M-1] & \cdots & \hat{r}_{y_i y_i}[M-p] \end{bmatrix} \begin{bmatrix} a_1 \\ \vdots \\ a_p \end{bmatrix} + e_i, \qquad (9)$$

$$i = 1, 2$$

where $e_i$, i=1,2, are the errors in eq. (7) introduced by the difference between the true auto-correlation function, $r_{y_i y_i}(n)$, i=1,2, and its estimate, $\hat{r}_{y_i y_i}(n)$, i=1,2, and $$x_i = \begin{bmatrix} \hat{r}_{y_i y_i}[q+1] \\ \vdots \\ \hat{r}_{y_i y_i}[M] \end{bmatrix}, i = 1, 2 \qquad (10)$$

$$H_i = \begin{bmatrix} \hat{r}_{y_i y_i}[q] & \cdots & \hat{r}_{y_i y_i}[q-p+1] \\ \vdots & \ddots & \vdots \\ \hat{r}_{y_i y_i}[M+1] & \cdots & \hat{r}_{y_i y_i}[M-p] \end{bmatrix}, i = 1, 2 \qquad (11)$$

$$\theta = \begin{bmatrix} a_1 \\ \vdots \\ a_p \end{bmatrix} \qquad (12)$$

The least-squares estimate gives the solution that minimizes $\|x_i - H_i \theta\|^2$, i=1,2.

The MA parameters $b_{i1}, \ldots, b_{iq}$ (i=1, 2) are identified by adopting the cross-relation algorithm used for FIR systems. The two outputs driven by the same input have the following cross-relation:

$$Y_1(z) H_2(z) = \frac{Y_1(z) B_2(z)}{A(z)} = \frac{B_1(z) Y_2(z)}{A(z)} = H_1(z) Y_2(z) \qquad (13)$$

Rewriting eq. (13) yields $$Y_1(z) B_2(z) - Y_2(z) B_1(z) = 0 \qquad (14)$$

The matrix form of Eq. (14) is $$[Y_1 \ -Y_2] \begin{bmatrix} B_2 \\ B_1 \end{bmatrix} \equiv Y \cdot B = 0 \qquad (15)$$

where $B_i \equiv [b_{iq}, \ldots, b_{i0}]^T$, i=1, 2 and $$Y_i \equiv \begin{bmatrix} y_i(0) & y_i(1) & \cdots & y_i(q) \\ y_i(1) & y_i(2) & \cdots & y_i(q+1) \\ \vdots & \vdots & \ddots & \vdots \\ y_i(N-q) & y_i(N-q+1) & \cdots & y_i(N) \end{bmatrix}^T, i = 1, 2$$

In the noise-free case, B is in the null space of the matrix Y. In the presence of sensor noise, the least-squares estimate gives the solution, within a scalar factor, that minimizes $\|Y \cdot B\|^2$.

A Modified Least-Squares BSI Algorithm Using an ARMA Model

In the least squares BSI algorithm for IIR systems, the dynamics of each channel are described by an ARMA model, i.e.:

$$H_i(z) = \frac{Y_i(z)}{U(z)} = \frac{B_i(z)}{A(z)}, i = 1, 2 \qquad (16)$$

where $A(z)$ is a $p^{th}$ order polynomial whose coefficients are identified based on the assumption that the input is white noise with zero mean. The form of $A(z)$ can be simplified for cardiovascular BSI by considering some features of circulatory system dynamics.

Figure 6:
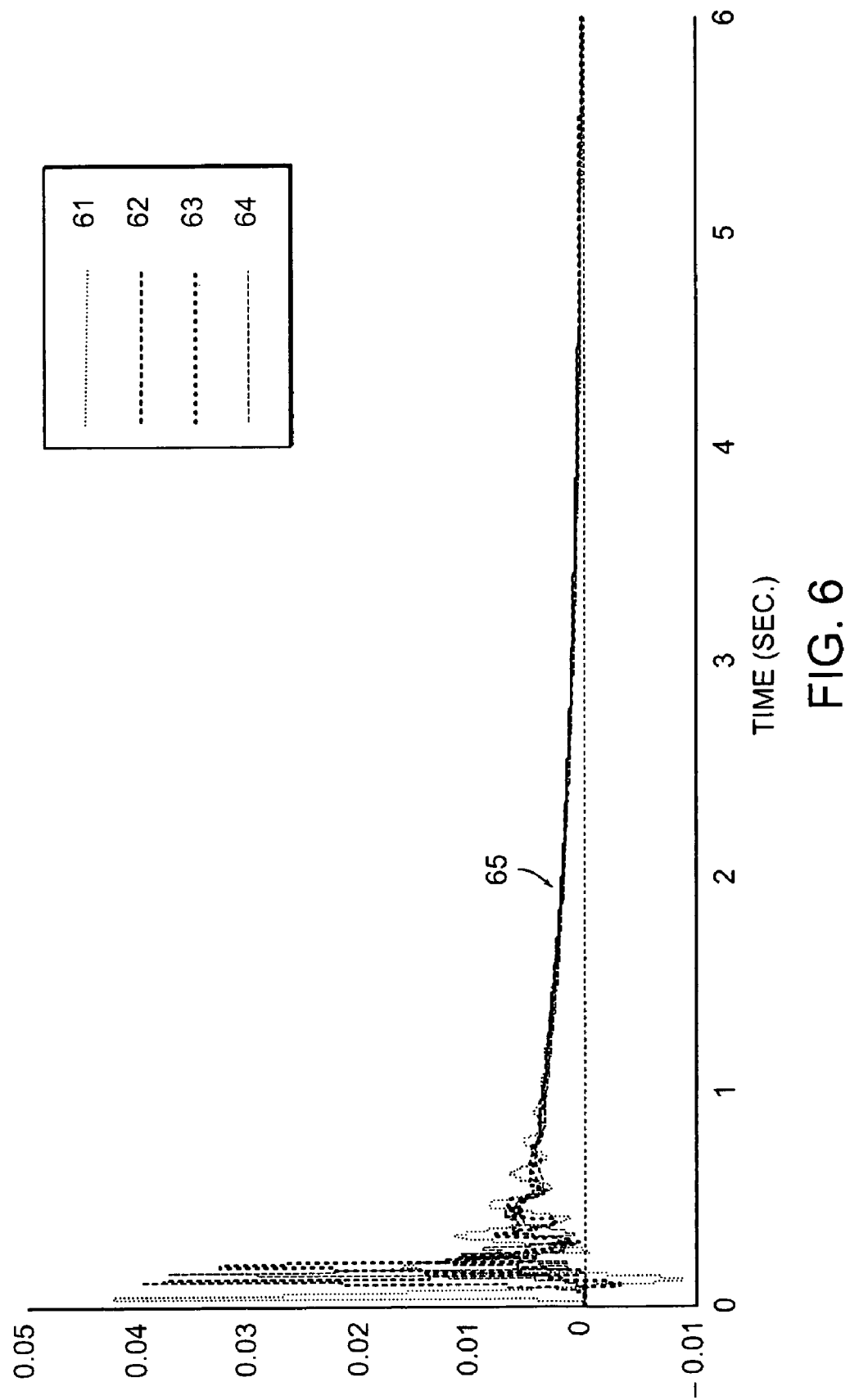
FIG. 6 depicts impulse responses for several channels from aortic blood flow to peripheral blood pressure.

As discussed earlier, one of the basic disadvantages of the FIR representation is that many parameters may be needed if the system has poles close to the unit circle, corresponding to slowly converging modes. In such a situation, the impulse response decays slowly, so the order of the FIR model is large to accurately approximate the system. Cardiovascular systems often show such behavior. FIG. 6 graphs the impulse responses of peripheral blood pressure, specifically carotid 61, brachial 62, femoral 63, and radial pressure 64, as a function of time. After some delays and oscillation, all the impulse responses 61, 62, 63, 64 overlap onto a long tail 65, which is due to an overall time constant of the circulatory system. Two factors that determine the decaying speed of the tail are the total arterial compliance and the total peripheral resistance, which are the characteristics of the entire cardiovascular system and are identical for all the arterial branches. Therefore, whenever a pressure transducer is placed on the periphery of a subject's cardiovascular system, the same 'tail effect' is observed. This 'tail effect' is a type of common dynamics of the cardiovascular system that is present in every channel's outputs. Not only does the 'tail effect' increase the order of the FIR approximation of each channel, but it also breaks one of the identifiability conditions for BSI algorithms.

Another observation concerning circulatory system dynamics is that the common slow-converging pole of each channel has the lowest natural frequency. In other words, the common pole converges slower than the poles that have higher natural frequencies.

Based on these observations, the system representations and algorithm previously developed for cardiovascular systems can be altered to create a modified least-squares BSI algorithm using an ARMA model.

The circulatory system dynamics can be represented by a new type of ARMA model, i.e.:

$$H_i(z) = \frac{Y_i(z)}{U(z)} = \frac{1}{1+az^{-1}} \cdot B_i(z) \equiv H_{LF}(z) \cdot H_{HFi}(z), i = 1, 2 \quad (17)$$

where $B_i(z)$, i=1, 2, are as defined in eq. (6). The first-order-polynomial AR part represents the common low-frequency slow-converging pole, while the higher-order-polynomial MA parts represents the high-frequency fast-converging poles. Since impulse responses due to those poles decay quickly, they can be described by FIRs. If the common pole can be identified independently from the channel outputs, the cross relation solution method described earlier can be used to identify $B_i(z)$, i=1, 2.

Figure 7:
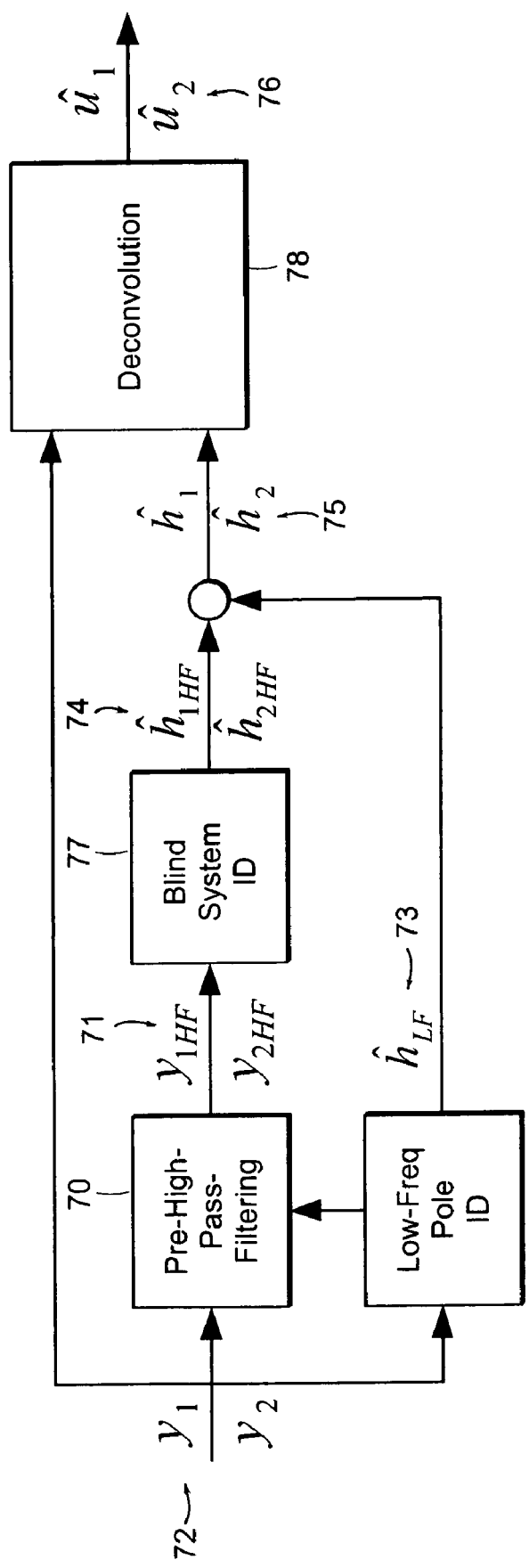
FIG. 7 provides a block diagram of cardiovascular multi-channel blind system identification.

A schematic showing elements of the new algorithm is presented in FIG. 7. From channel outputs 72 $y_1$, $y_2$, the common low-frequency pole is estimated using time decay method or area method, as described by Stergiopulos, N., et al., "Evaluation of methods for estimation of total arterial compliance," *American Journal of Physiology, Heart Circulatory Physiology*, Vol. 268, No. 37, pp. H1540–H1548 (1995), which is incorporated herein by reference.

The outputs 72 are filtered by a pre-high-pass filter 70 designed based on the equation:

$$H_{HP}(z) = \frac{1+az^{-1}}{1+\beta az^{-1}}, \beta < 1 \quad (18)$$

The pre-filtered outputs 71 $y_{1HF}, y_{2HF}$ are fed into the cross-relation BSI algorithm 77 to identify the high-frequency impulse responses 74 $\hat{h}_{1HF}, \hat{h}_{2HF}$. Combining the low-frequency response 73 and high-frequency responses 74 give the complete impulse response estimates 75 $\hat{h}_1, \hat{h}_2$. The input 76 is then identified by deconvolving 78 the outputs 72 and estimated impulse response 75.

The procedure for cardiovascular multi-channel blind system identification is summarized as follows:

1. Estimate the common low-frequency pole from multiple system outputs;
2. Design the pre-high-pass filter based on the low-frequency pole estimation;
3. Filter the multiple outputs by the pre-high-pass filter;
4. Estimate the high-frequency impulse response from the pre-filtered outputs;
5. Get the complete impulse response by combining the low-frequency and high-frequency impulse responses;
6. Estimate the system input from multiple system outputs and the estimated system functions.

The modified least-squares BSI algorithm for ARMA systems was tested on a simulated multi-channel system, whose channel dynamics simulate those of the radial, femoral, brachial, and carotid branches; the numerical cardiovascular simulator is described in U.S. Pat. No. 6,117,087, which is incorporated by reference herein. The 30-element simulator generates flow, pressure, velocity, and area signals at different locations of a cardiovascular system. Aortic flow is the input to be estimated; cardiac output is the integration of aortic flow over one minute. The branches that are of the greatest interest are the carotid, the brachial, the radial, and the femoral because they can be easily accessed for noninvasive measurements.

Figure 8:
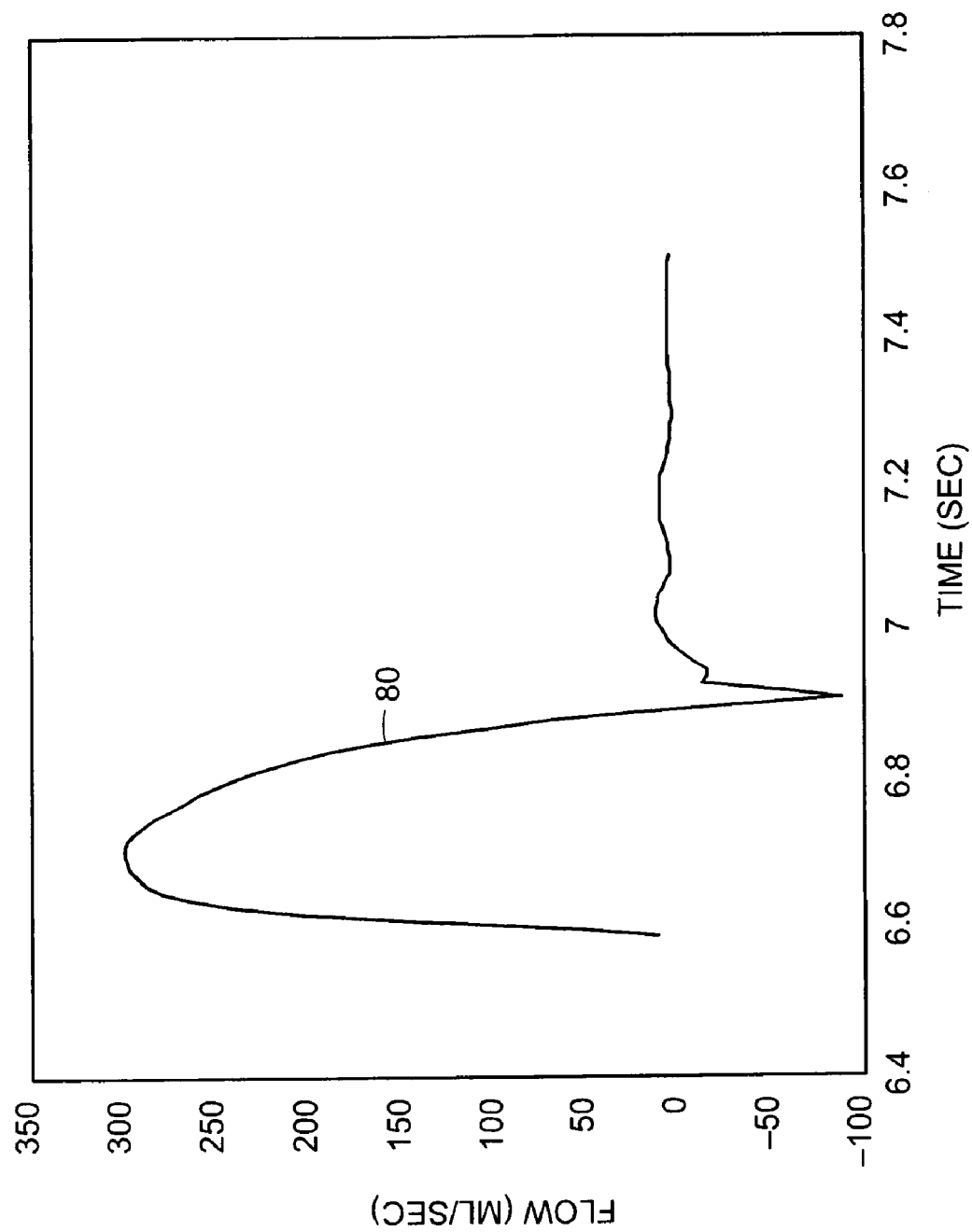
FIG. 8 provides a graph of the system input, aortic blood flow, as a function of time for a multi-channel BSI simulation.
Figure 9:
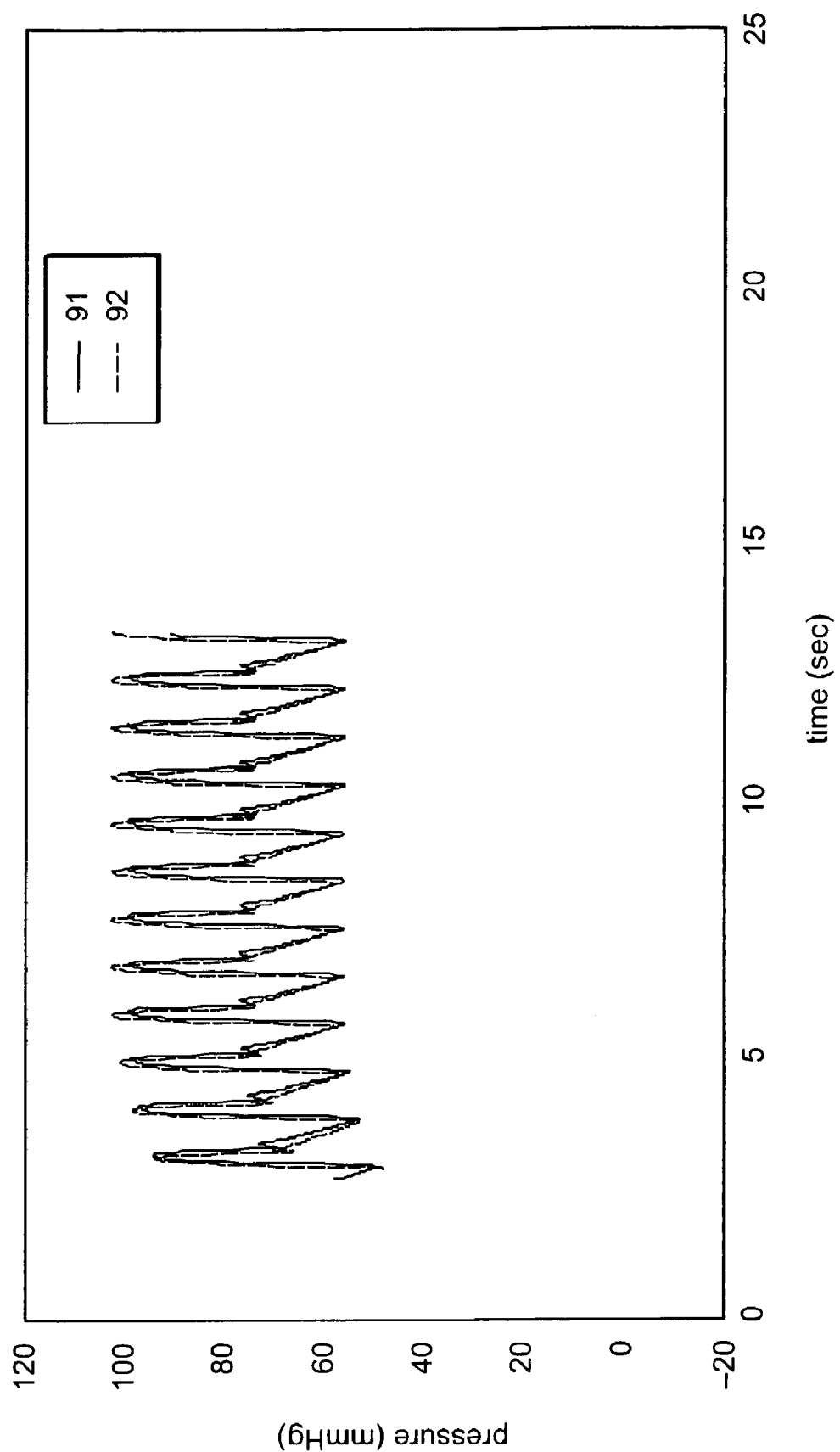
FIG. 9 provides a graph of system outputs, femoral and brachial blood pressure, as a function of time for a multi-channel BSI simulation.
Figure 10:
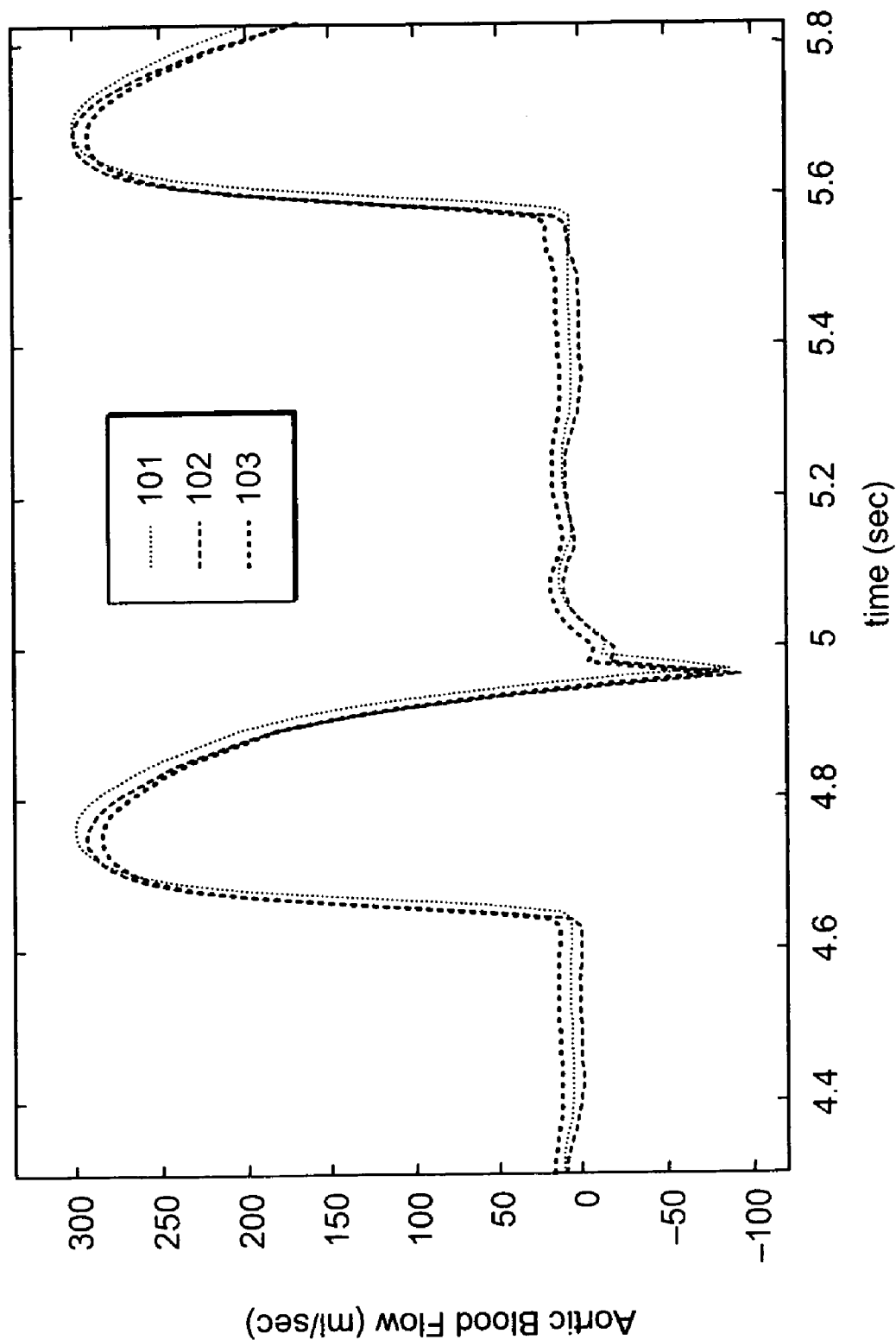
FIG. 10 provides a graph of estimates of aortic blood flow, based on the femoral and brachial channels, and the aortic blood flow from a simulation, as a function of time.

In this test, only the data from the femoral and brachial channels are utilized. The simulated system input to be modeled 80, aortic blood flow, is graphed as a function of time in FIG. 8. The system outputs, femoral 91 and brachial blood pressure 92, are graphed as a function of time in FIG. 9. The time constant corresponding to the low-frequency pole is estimated using the area method, and is estimated as $t_c$=1.5335 sec. The pre-high-pass filter is then designed and the pre-filtered outputs calculated. The high-frequency responses of the two channels are then estimated from the pre-filtered output using the cross relation solution method. The complete estimated femoral and brachial channel responses are then calculated. Finally, the input is identified from the estimated impulse response and the output of each channel using deconvolution. FIG. 10 presents plots of the measured aortic blood flow 101, the estimated aortic blood flow based on the femoral channel data 102, and the estimated aortic blood flow based on the brachial channel data 103, as a function of time. The estimates 102, 103 capture the major features of the input 101.

Intermediate Input Identification Algorithm

The modified least-squares BSI algorithm using an ARMA model improves the impulse response estimates by removing a piece of each channel's function, the first-order AR part, that is common to all channels. The piece is referred to as the common dynamics of the impulse response of each channel. The remaining part of the impulse response for each channel is referred to as the distinct dynamics of the channel. When the common dynamics are at low frequencies, however, a high-pass-filter applied to the outputs tends to amplify signal noise. Thus, the algorithm has the disadvantage of being prone to noise amplification when the common dynamics are at low frequency. As well, if there exist distinct dynamics in the same frequency range as the common dynamics, direct filtering will change the distinct dynamics in all the channels. Another method, named the Intermediate Input IDentification (IIID) algorithm, is developed to address these potential problems.

The impulse response of each channel, also known as the channel dynamics, is decomposed into two parts: common dynamics, whose transfer function is denoted by $H_0(z^{-1})$, and distinct dynamics, whose transfer functions for two channels are denoted by $H_1'(z^{-1})$ and $H_2'(z^{-1})$ respectively. $H_1(z^{-1})$ and $H_2(z^{-1})$ represent the overall transfer functions of the two channels respectively, i.e.:

$$H_i(z^{-1})=H_i'(z^{-1})H_0(z^{-1}), i=1,2 \tag{19}$$

If the system is linear, the two-channel system can be rearranged because of the interchangeability of linear dynamics. The dynamic equations of the new multi-channel system in the frequency domain are:

$$\begin{aligned} Y_i(z^{-1}) &= H_i(z^{-1})U(z^{-1}) \\ &= [H_i'(z^{-1})H_0(z^{-1})]U(z^{-1}) \\ &= H_i'(z^{-1})[H_0(z^{-1})U(z^{-1})] \\ &= H_i'(z^{-1})V(z^{-1}), \; i=1,2 \end{aligned} \tag{20}$$

The outputs of a multi-channel system are correlated since both channels are driven by the same input. This is also true for systems with common dynamics. When the cross relation solution method is applied to the outputs of a system with common dynamics, under certain conditions described herein, the channel dynamics are distinct to each channel, e.g., $H_1'(z^{-1})$ and $H_2'(z^{-1})$. In other words, the distinct dynamics can be uniquely identified even when common dynamics are present. This leads to the introduction of a new variable, the intermediate input $v(n)$, and the IIID algorithm to the multi-channel BSI problem for systems with common dynamics. The main idea is to treat the common dynamics as part of the input. The intermediate variable, $v(n)$, whose z-transform is denoted by $V(z^{-1})$, is treated as the input to the multi-channel system.

The IIID algorithm solves the multi-channel BSI problem when common dynamics are present in two steps. The first is to solve the distinct dynamics from the outputs. The distinct dynamics can be uniquely solved up to a scalar factor from the outputs even when common dynamics are present, as described in Y. Zhang, "Multi-channel Blind System Identification for Central Hemodynamic Monitoring," MIT Ph.D. Thesis, Department of Mechanical Engineering, MIT (2002), which is incorporated herein by reference. For a two-channel problem, assuming that there is no noise and the input $v(n)$ has a linear complexity of order $2L_d-1$, where $L_d$ is the maximum order of the channels (defined above with reference to eq. (2)), the only solution to eq. (4) as applied to the distinct dynamics is $W_1$ and $W_2$ whose elements are the coefficients of the following polynomials:

$$W_1(z^{-1})=\alpha H_1'(z^{-1})$$

$$W_2(z^{-1})=\alpha H_2'(z^{-1})\theta_{\Delta K}(z^{-1}) \tag{21}$$

where $\alpha$ is an arbitrary constant, $\theta_{\Delta K}(z^{-1})=z^{-\Delta K}$, and $\Delta K$ is the difference in the orders of the two channels, when the order of channel 1 is greater than or equal to the order of channel 2.

The distinct dynamics may be obtained using any appropriate technique known to those skilled in the art, including, but not limited to, multi-channel BSI algorithms. As well, the IIID algorithm allows a different set of AR parameters for each channel when an ARMA model is used for the impulse response, unlike what is required in the least-squares BSI algorithm and the modified least-squares BSI algorithm.

The second step is to determine the common dynamics from the intermediate variable $v(n)$ by exploiting the zero-input response. The common dynamics and the input are combined and the new intermediate variable $v(n)$ is treated as the input to the multi-channel system that has no common factor.

Figure 11:
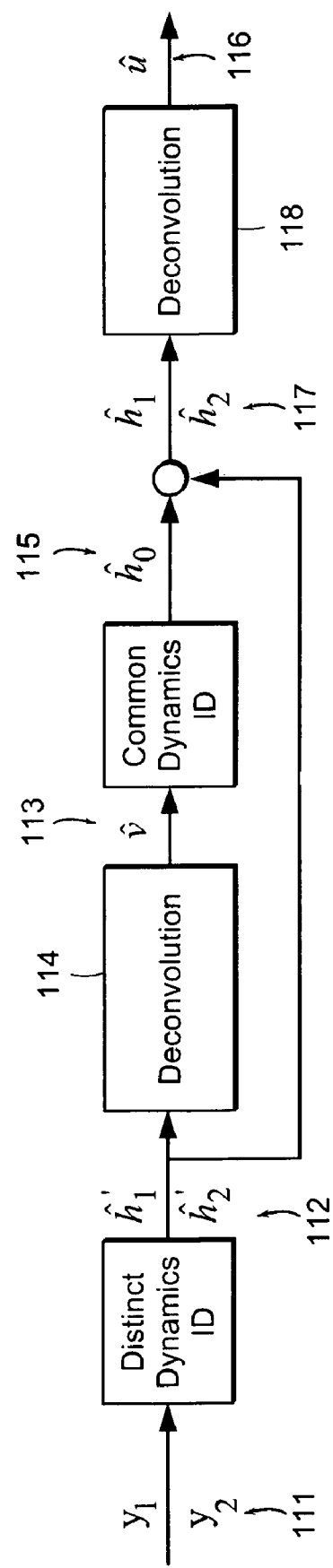
FIG. 11 provides a flow chart of the Intermediate Input ID approach.

A flow chart of the elements of the algorithm is shown in FIG. 11. The procedural steps are:
1. Identify the distinct dynamics 112 from the outputs $y_1$, $y_2$ using existing multi-channel BSI algorithms;
2. Estimate the intermediate variable $v(n)$ 113 by deconvolving 114 the estimated distinct dynamics 112 from the outputs 111;
3. Identify the common dynamics 115 from the intermediate input $v(n)$ 113 by exploiting the zero-input response of the common dynamics;
4. Estimate the complete dynamics 117 by combining the common dynamics 115 and the distinct dynamics 112;
5. Estimate the input $u(n)$ 116 by deconvolving 118 the estimated complete dynamics 117 from the outputs 111.

Alternatively for final step, the input $u(n)$ may be obtained by deconvolving the common dynamics from the estimated intermediate input $v(n)$.

The algorithm has been formulated for a two-channel problem herein. Those skilled in the art, however, can extrapolate the algorithm for systems with a greater number of channels.

Combining the requirements for the distinct dynamics identification and the common dynamics identification, the system must satisfy the following conditions to be identifiable:

The output must have enough samples available.

The intermediate input $v(n)$ must excite all the modes in the distinct dynamics.

The original input $u(n)$ must excite all the modes in the common dynamics.

The input must be zero for a sufficiently long period.

No common zeros are present.

Estimation of the Channel Order

Most multi-channel BSI algorithms require a priori knowledge of the channel order, which is not always conveniently available in practice. Herein a procedure is described for identifying the maximum channel order of the distinct dynamics of a set of channels. When the maximum order of the distinct dynamics of the two channels, i.e. $L_d=\max(L_1, L_2)$, is unknown, an overestimated upper limit of the maximum order, $L_e$, is chosen such that $L_e=L_d+\Delta K$. The solutions to eq. (4), using $L_d$ as the maximum order, follow:

$$Y(L)\begin{bmatrix} W_1(L) \\ W_2(L) \end{bmatrix} \equiv [Y_2(L), -Y_1(L)]\begin{bmatrix} W_1(L) \\ W_2(L) \end{bmatrix} = 0 \tag{22}$$

where $W_1(z^{-1}), W_2(z^{-1})$ are polynomials with higher orders than $H_1'(z^{-1}), H_2'(z^{-1})$, which are related by $$W_1(z^{-1}) = \alpha H_1'(z^{-1}) \theta_1(z^{-1})$$

$$W_2(z^{-1}) = \alpha H_2'(z^{-1}) \theta_1(z^{-1}) \theta_{\Delta K}(z^{-1}) \quad (23)$$

where $\alpha$ is an arbitrary constant, $\theta_{\Delta K}(z^{-1}) = z^{-\Delta K}$ and $\theta_1(z^{-1})$ is a polynomial of order K whose roots are at arbitrary locations.

The locations of the extraneous roots of $W_1(z^{-1}), W_2(z^{-1})$ have the following property: the two channels have exactly the same extraneous roots, except that the one with the larger order has all of its additional extraneous roots at the origin. In the noiseless case, the matrix $Y(L_e)$ defined as $$Y(L_e) = [Y_2(L_e), -Y_1(L_e)] = [V(L_e) \cdot H_2'(L_e), -V(L_e) \cdot H_1'(L_e)]$$
$$= [V(L_e) \cdot H_2'(L_e), -H_1'(L_e)] = \{U(L_e) \cdot H_0(L_e)\} \cdot [H_2'(L_e), -H_1'(L_e)] \quad (24)$$

where $$Y_i(L_e) \equiv \begin{bmatrix} y_i(L_e) & \cdots & y_i(2L_e - 1) \\ \vdots & \ddots & \vdots \\ y_i(N - L_e + 1) & \cdots & y_i(N) \end{bmatrix} : \{(N - 2L_e + 2) \times L_e\}, i = 1, 2 \quad (25)$$

$$H_i'(L_e) \equiv \begin{bmatrix} h_2'(L_d) & & & & \\ \vdots & \ddots & & & \\ h_2'(1) & \cdots & h_2'(L_d) & & \\ & \ddots & \vdots & h_2'(L_d) & \\ & & h_2'(1) & \vdots & \ddots \\ & & & h_2'(1) & h_2'(L_d) \\ & & & & \ddots & \vdots \\ & & & & & h_2'(1) \\ \hline & & & K & & \end{bmatrix} : \{(2L_e - K - 1) \times L_e\}, i = 1, 2 \quad (26)$$

$$V(L_e) \equiv \begin{bmatrix} v(K+1) & \cdots & v(2L_e - 1) \\ \vdots & \ddots & \vdots \\ v(N - 2L_e + K + 2) & \cdots & v(N) \end{bmatrix} : \{(N - 2L_e + 2) \times (2L_e - K - 1)\} \quad (27)$$

$$H_0(L_e) \equiv \begin{bmatrix} h_0(L_c) & & & \\ \vdots & \ddots & & \\ h_0(1) & \cdots & h_0(L_c) & \\ & \ddots & \vdots & \ddots \\ & & h_0(1) & h_0(L_c) \\ & & & \ddots & \vdots \\ & & & & h_0(1) \end{bmatrix} : \{(2L_e - K + L_c - 2) \times (2L_e - K - 1)\} \quad (28)$$

$$U(L_e) \equiv \begin{bmatrix} u(K - L_c + 2) & \cdots & u(2L_e - 1) \\ \vdots & \ddots & \vdots \\ u(N - 2L_e + K - L_c + 3) & \cdots & u(N) \end{bmatrix} : \{(N - 2L_e + 2) \times (2L_e - K + L_c - 2)\} \quad (29)$$

has K zero singular values. If there is additive noise, then $Y(L_e)$ is of full rank. However, if the number of input samples, N, is reasonably large, the K+1 smallest eigenvalues are close to the square root of the noise power density, as described by H. Liu, G. Xu, and L. Tong, "A deterministic approach to blind equalization," Conference Record of The Twenty-Seventh Asilomar Conference on Signals, Systems and Computers, Vol. 1, pp. 751–755 (1993), which is incorporated herein by reference. These singular values are typically noise singular values.

Therefore, by checking how many smaller singular values of $Y(L_e)$ are close to one another, K+1 can be determined, and thus $L_d$. More objective criteria and other detection methods, as known to those skilled in the art, can also be used to detect $L_d$.

The procedure for maximum channel order estimation is the following:

Overestimate the channel order as $L_e$;
Formulate the matrix $Y(L_e)$ from the signals observed;
Calculate the singular values of $Y(L_e)$;
Based on the knowledge of the noise level, estimate how many smaller singular values are the noise singular value and estimate the maximum channel order;
Use the estimated maximum channel order, $\hat{L}_d$, to formulate $Y(\hat{L}_d)$;
Obtain the least-squares estimation of the distinct dynamics from the singular vector corresponding to the smallest singular value of $Y(\hat{L}_d)$.

Though the maximum channel order estimation procedure described herein is applied to the problem of estimating the channel order for the distinct dynamics in the IIID approach, the procedure may also be applied to the multi-channel BSI algorithms that do not use the IIID approach when the channel order is unknown. As well, the technique is easily extrapolated in the context of having more than two channels of outputs.

Common Dynamics Formulation

To solve the common dynamics from v(n), the zero-input response of the system is utilized. The common dynamics may be described by:

$$x(n+1) = Fx(n) + Gu(n)$$

$$v(n) = Jx(n) \quad (30)$$

where x is the array of state variables, F, G, and J are matrices with proper dimensions. The response of the system v(n) consists of two components: the zero-input response and the zero-state response. The zero-input response is the response due to the non-zero initial condition when the input is zero. The zero-state response is the response due to the input when the initial condition is zero. If $V(z^{-1})$ and $U(z^{-1})$ are the z-transforms of the corresponding signals v(n) and u(n), respectively, they have the relation:

$$V(z^{-1}) = [Jz(zI-F)^{-1}]x(0) + [J(zI-F)^{-1}G]U(z^{-1}) \tag{31}$$

where x(0) is the initial condition of the state variables. The left and right terms on the right-hand side of eq. (31) correspond to the zero-input response and the zero-state response, respectively. If the input is zero for a certain time, the right term disappears. Then the modes in the common dynamics can be identified from v(n) given that they have been excited. Since the zero-input response does not contain the information about the matrix G, i.e., the information about the zero locations, only the pole locations can be obtained from the zero-input response.

If the common dynamics between u(n) and v(n) are described by the following ARMA model:

$$v(n) = \sum_{k=0}^{m_0} b_{0,k} u(n-k) + \sum_{k=1}^{n_0} a_{0,k} v(n-k) \tag{32}$$

the moving average coefficients, $b_{0,k}$, k=1, . . . , $m_0$, will disappear when u(n) is zero. Only the auto-regressive coefficients, $a_{0,k}$, k=1, . . . , $n_0$, can be identified from the zero-input dynamics by solving the following linear equations:

$$\begin{bmatrix} v(t_0) \\ v(t_0+1) \\ \vdots \\ v(N) \end{bmatrix} = \begin{bmatrix} v(t_0-1) & \cdots & v(t_0-n_0) \\ v(t_0) & \cdots & v(t_0-n_0+1) \\ \vdots & \ddots & \vdots \\ v(N-1) & \cdots & v(N-n_0) \end{bmatrix} \begin{bmatrix} a_{0,1} \\ a_{0,2} \\ \vdots \\ a_{0,n_0} \end{bmatrix} \tag{33}$$

where u(n)=0 for n=$t_0$, . . . , N.

This condition is met for the arterial system due to the intermittent pumping action of the heart: the entire stroke volume is discharged into the systemic circulation during systole, which usually occupies only about one third of the cardiac cycle.

Figure 12:
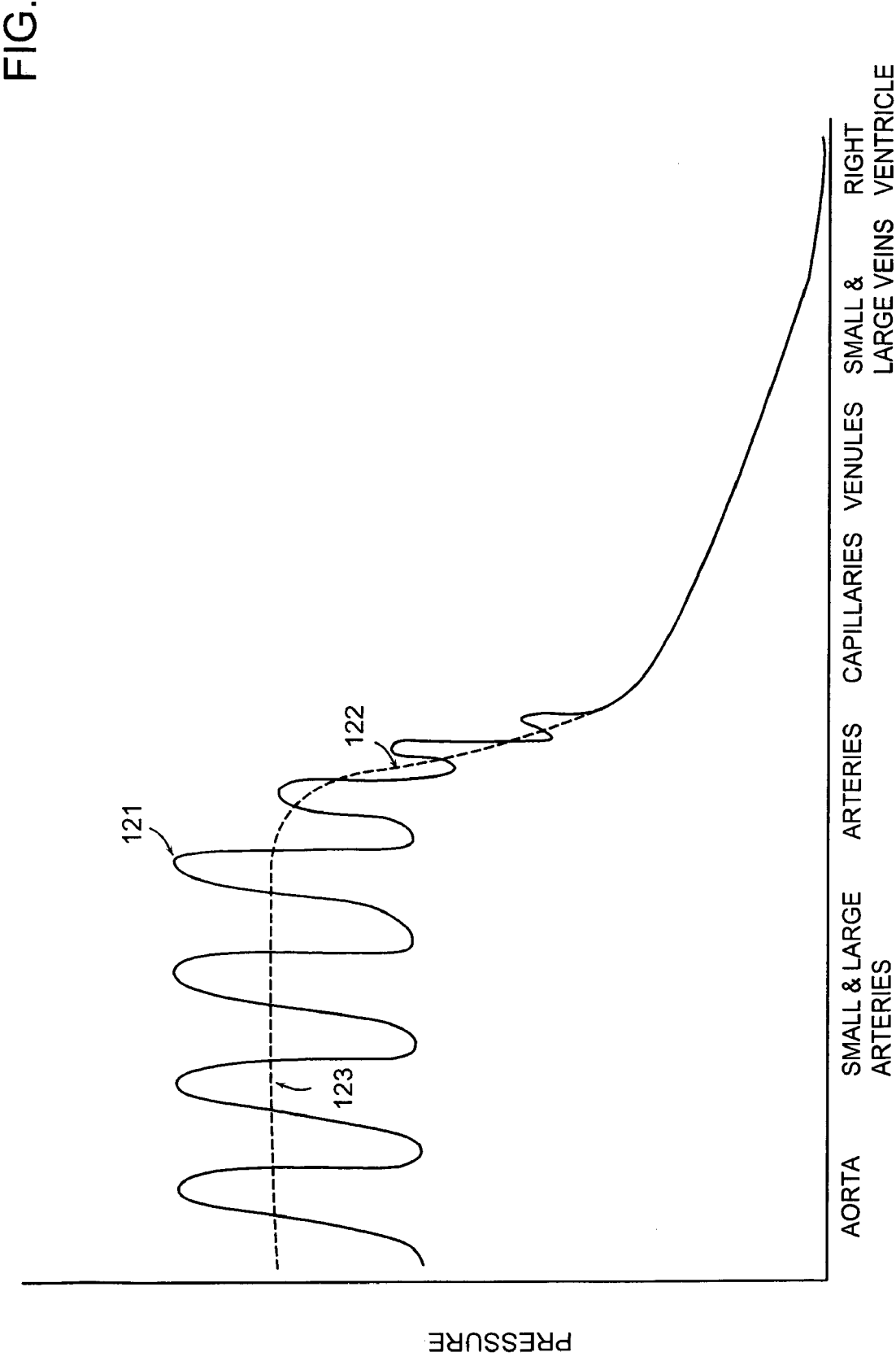
FIG. 12 depicts blood pressure at various locations in the cardiovascular system.

FIG. 12 depicts the blood pressure in various parts of the cardiovascular system. The solid line 121 depicts the actual blood pressure, which has an oscillatory behavior due to the systolic and diastolic parts. The dashed line 122 indicates the mean blood pressure. The mean arterial pressure 123 is almost preserved in the arteries. Therefore, the factors that determine the level of the mean arterial pressure are common for any arterial branches. The common dynamics are thus attributed to the arterial compliance and peripheral resistance, which determine the level of mean arterial pressure and the rate that the mean arterial pressure changes. This models the lumped-parameter nature of the circulatory system. In fact, the average behavior of the arterial system as a whole can be modeled as a compliance and resistance in parallel; models of this type are described in Welkowitz, W., *Engineering Hemodynamics: Application to Cardiac Assist Devices*, $2^{nd}$ Edition, New York University Press, New York (1987), which is incorporated herein by reference. The overall time constant of the arterial system is determined by the product of the total arterial compliance and the total peripheral resistance.

Results Using the IIID Approach

Figure 13:
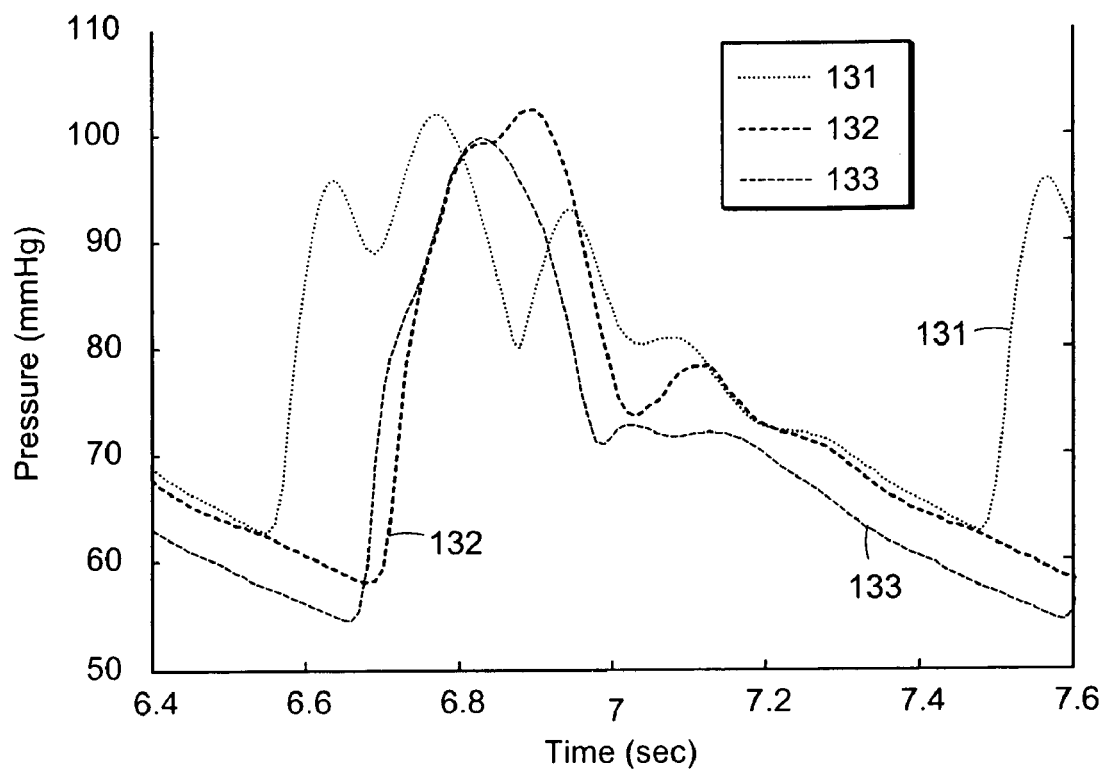
FIG. 13 depicts the output pressure of the carotid, femoral, and radial branches from a cardiovascular simulation.
Figure 14:
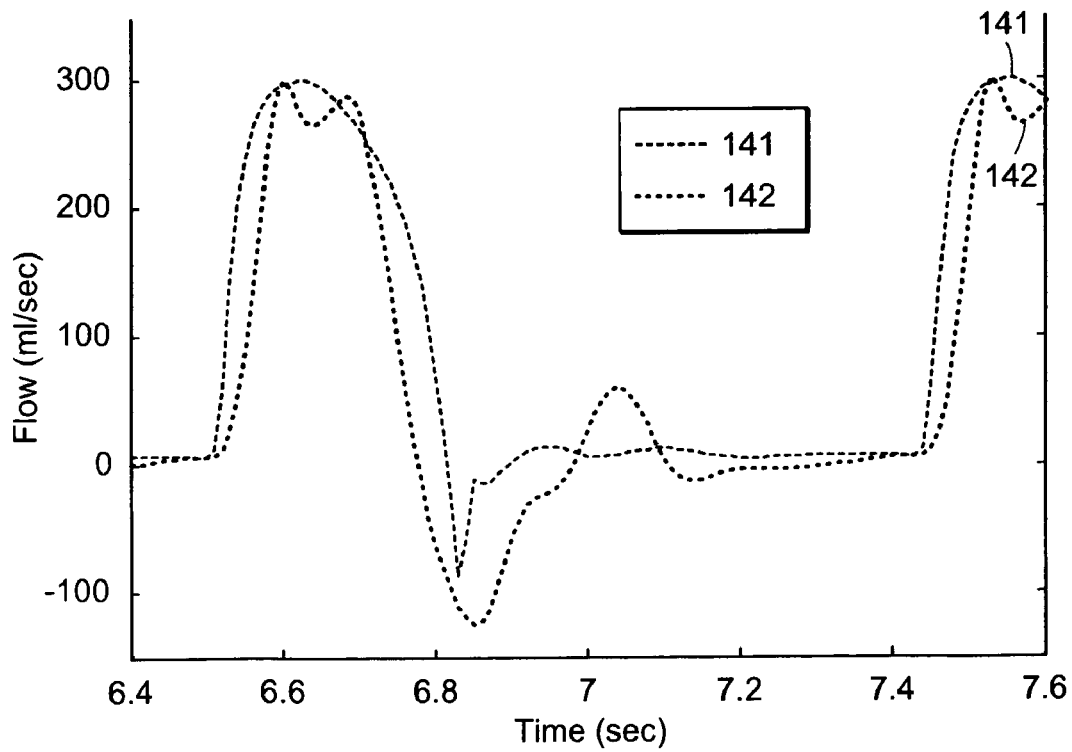
FIG. 14 plots the estimated aortic flow based upon the IIID algorithm and the aortic flow from a cardiovascular simulation, as a function of time.

The IIID embodiment was tested on a set of pressure signals generated by the cardiovascular simulator described earlier. In all the simulations, three channels were modeled by the ARMA representation; the signals were sampled at 100 Hz. The simulated pressures in the carotid 131, femoral 132, and radial 133 branches, as a function of time, are plotted in FIG. 13. Since the cardiovascular simulator is distributed and nonlinear, the system order was unknown and the maximum channel order estimation procedure was implemented to estimate the channel orders. FIG. 14 plots the aortic blood flow, as determined by the simulator 142 and as determined by the IIID algorithm 141 using an ARMA model to capture the distinct dynamics, as a function of time.

The IIID estimation of the aortic flow from three pressure tracings captures major features on the simulated aortic flow waveform. A delay exists between the simulated and IIID determined aortic blood flows due partially to a common delay shared by all the channels. This delay is removed in the graph shown in FIG. 14. The IIID approach cannot identify the common delay presented in the system since they are common zeros. The delay, however, can be removed using an electrocardiogram signal, which serves as a reference to align the estimation to the simulated dynamics. This technique can also be used to remove the delay when estimating the dynamics of a cardiovascular system.

Figure 15:
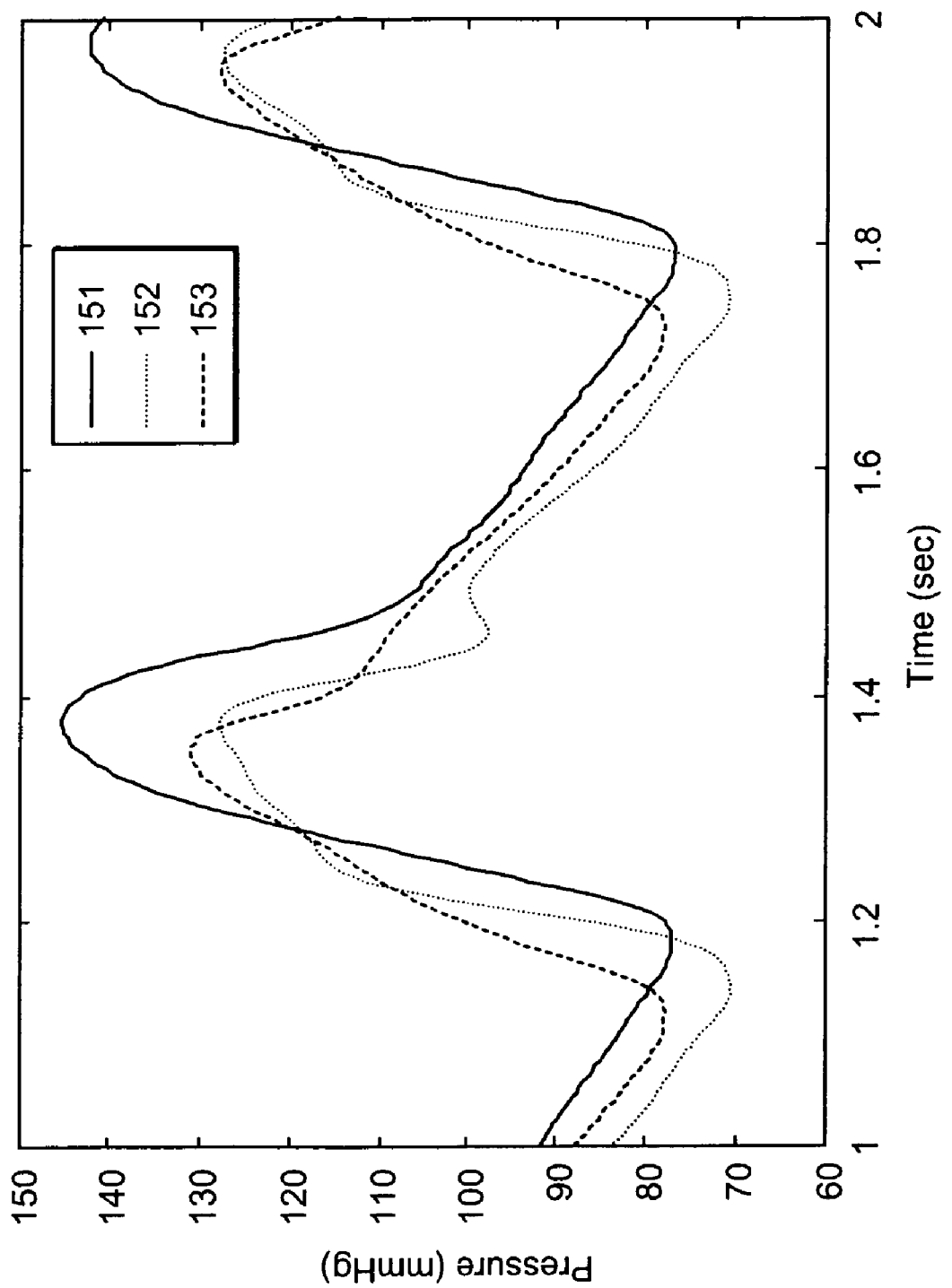
FIG. 15 provides a graph of pressure measurements as a function of time in the femoral, radial, and aortic arteries of a Yorkshire pig.
Figure 16:
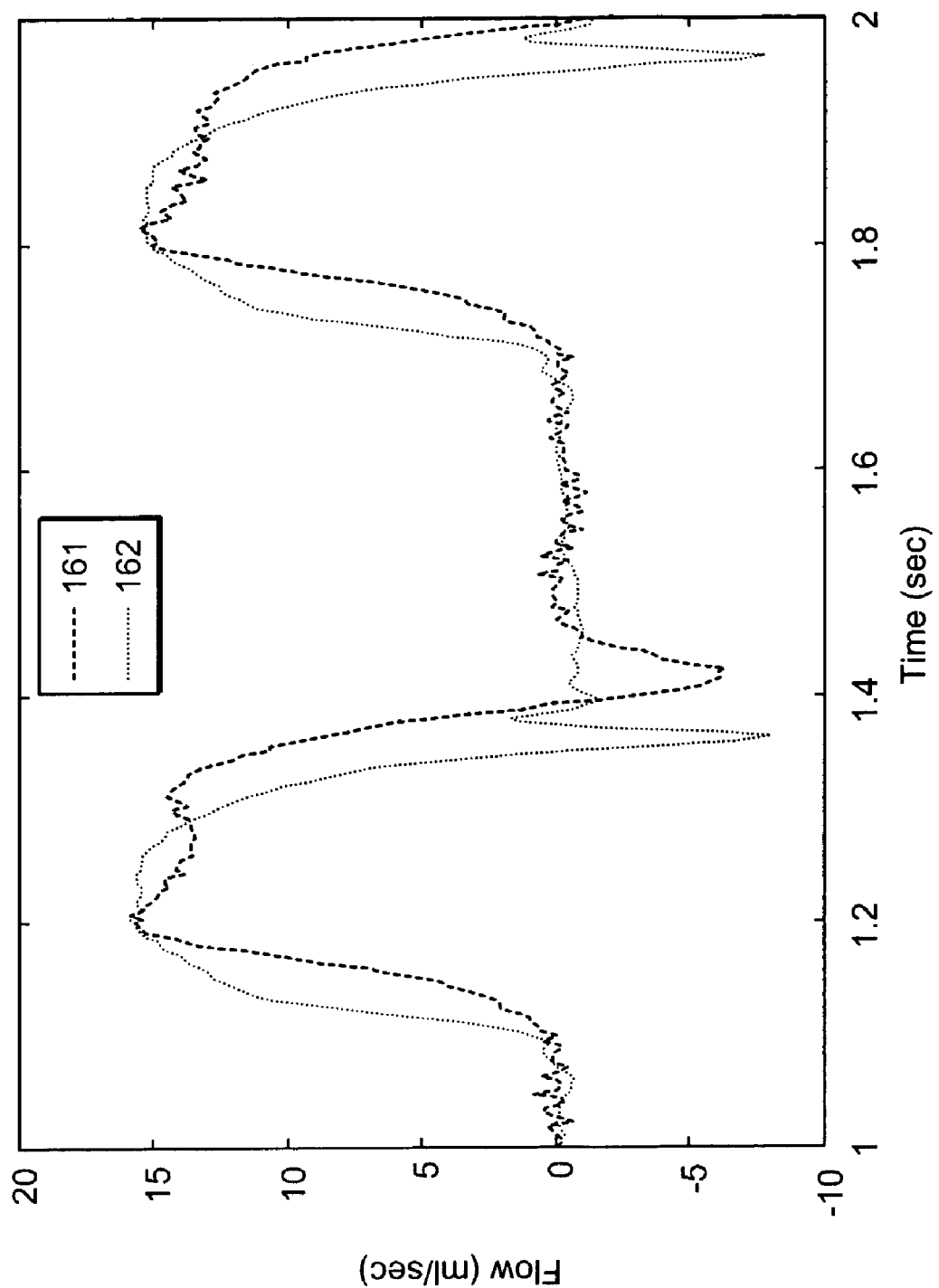
FIG. 16 provides a graph of the estimated aortic flow and the measured aortic flow, as a function of time, in a Yorkshire pig.

In addition, three channels of data, aortic, femoral and radial, taken from a Yorkshire pig are modeled using an ARMA representation. Three pressure signals from the femoral 151, radial 152, and aortic 153 branches as a function of time are plotted in FIG. 15. The IIID algorithm was implemented with the maximum channel order estimation procedure. The impulse responses from each of the three channels were estimated, along with the intermediate variable using an ARMA model. Next, after the common dynamics are estimated, the input, aortic blood flow, can be deconvoluted. FIG. 16 plots the aortic blood flow, from the IIID algorithm 161 and as measured in the pig 162, as a function of time. The major features of the actual aortic flow 162 are modeled by the IIID estimation 161.

Computer Implementation of Embodiments

In alternative embodiments, the disclosed methods for determining a system input from non-invasive system output measurements may be implemented as a computer program product for use with a computer system. Such implementations may include a series of computer instructions fixed either on a tangible medium, such as a computer readable medium (e.g., a diskette, CD-ROM, ROM, or fixed disk) or transmittable to a computer system, via a modem or other interface device, such as a communications adapter connected to a network over a medium. The medium may be either a tangible medium (e.g., optical or analog communications lines) or a medium implemented with wireless techniques (e.g., microwave, infrared or other transmission techniques). The series of computer instructions embodies all or part of the functionality previously described herein. Those skilled in the art should appreciate that such computer instructions can be written in a number of programming languages for use with many computer architectures or operating systems. Furthermore, such instructions may be stored in any memory device, such as semiconductor, magnetic, optical or other memory devices, and may be transmitted using any communications technology, such as optical, infrared, microwave, or other transmission technologies.

It is expected that such a computer program product may be distributed as a removable medium with accompanying printed or electronic documentation (e.g., shrink wrapped software), preloaded with a computer system (e.g., on system ROM or fixed disk), or distributed from a server or electronic bulletin board over a network (e.g., the Internet or World Wide Web). Of course, some embodiments of the invention may be implemented as a combination of both software (e.g., a computer program product) and hardware. Still other embodiments of the invention are implemented as entirely hardware, or entirely software (e.g., a computer program product).

All aforementioned embodiments of the invention are intended to be merely exemplary and numerous variations and modifications will be apparent to those skilled in the art. All such variations and modifications are intended to be within the scope of the present invention as defined in the appended claims.

We claim:

1. A method for evaluating cardiac performance in a body of a subject having a circulatory system, the method comprising:
   (a) measuring outputs of a plurality of sensors, each sensor deployed at a site of the circulatory system of the subject and providing a signal constituting a channel, each channel having an output;
   (b) collecting a plurality of channel outputs from the plurality of channels at specified instants of time;
   (c) expressing the plurality of channel outputs in terms of a finite set of auto-regression parameters by recursive solution of an estimation model for auto-correlation functions, thereby estimating an impulse response and transfer function for each channel;
   (d) estimating an input by deconvolution based on the estimated impulse response and the plurality of channel outputs to provided an indication of cardiac performance; and
   (e) updating the finite set of auto-regression parameters based on continued performance of steps (a), (b), (c), and (d) in which new data points are included and earlier data points are disregarded.

2. A method in accordance with claim 1, wherein the step of measuring includes determining peripheral pressure at a plurality of peripheral sites of the circulatory system.

3. A method in accordance with claim 1, wherein the step of expressing the plurality of channel outputs in terms of the finite set of auto-regression parameters includes solution using a least-squares algorithm.

4. A method in accordance with claim 1, wherein the step of expressing the plurality of channel outputs in terms of the finite set of auto-regression parameters includes estimating a maximum order of the auto-correlation functions by:
   (a) over-estimating the maximum order of the auto-correlation functions;
   (b) estimating an impulse response and transfer function for each channel based upon the overestimated maximum order; and
   (c) estimating the maximum order of the auto-correlation functions using common singular values of the estimated impulse response and transfer function for each channel based upon the overestimated maximum order.

5. A method in accordance with claim 1, wherein the step of expressing the plurality of channel outputs in terms of the finite set of auto-regression parameters includes assumption of a transfer function separable into a product of a low-frequency and a high-frequency component.

6. A method in accordance with claim 5, further comprising:
   (a) estimating a common low-frequency pole from the plurality of channel outputs;
   (b) filtering the plurality of channel outputs using a pre-high-pass filter, based on the estimated common low-frequency pole and impulse response, to obtain pre-filtered outputs;
   (c) estimating a high-frequency impulse response based on the pre-filtered outputs; and
   (d) combining the low-frequency impulse response and the high-frequency impulse response to obtain a complete estimated impulse response.

7. A method in accordance with claim 1, wherein the step of expressing the plurality of channel outputs in terms of the finite set of auto-regression parameters is based on an infinite impulse response representation of the circulatory system.

8. A method in accordance with claim 1, wherein the input is an intermediate input that includes common dynamics of the plurality of channels, and the finite set of auto-regression parameters includes subsets of auto-regression parameters that are each unique to a particular channel, the method further comprising:
   (a) estimating the common dynamics of the plurality of channels based at least in part upon the intermediate input;
   (b) estimating a system input by deconvolution based on the common dynamics; and
   (c) updating the estimates of the common dynamics and system input based upon the updated finite set of auto-regression parameters.

9. A method in accordance with claim 8, wherein the step of estimating the common dynamics of the plurality of channels includes using outputs of the plurality of sensors corresponding substantially to a diastole of a cardiac cycle.

10. A method in accordance with claim 8, wherein the step of estimating the common dynamics of the plurality of channels includes assuming the plurality of channels have a common low-frequency pole.

11. A method in accordance with claim 8, wherein the step of estimating the system input includes using an electrocardiogram signal.

12. A computer program product embodied on a computer readable medium for use on a computer system for estimating a system input from a plurality of system outputs, the computer program product including computer readable program code including:
   (a) module for collecting signals from a plurality of sensors at specified instants of time, the signals corresponding to a measured set of system outputs, each signal constituting a channel;
   (b) program code for expressing the signals in terms of a finite set of auto-regression parameters by recursive solution of an estimation model for auto-correlation functions, and thereby estimating an impulse response and transfer function for each channel;
   (c) program code for estimating an input by deconvolution based on the estimated impulse response and the signals from the plurality of sensors; and
   (d) a routine for updating the input by continued collection of signals from the plurality of sensors and continued execution of the program code in steps (b) and (c) that utilize new signals and disregard earlier signals.

13. A computer program product in accordance with claim 12, wherein the system outputs and the input refer to a body of a subject having a circulatory system.

* * * * *